(12) United States Patent
De Jong et al.

(10) Patent No.: US 11,622,890 B2
(45) Date of Patent: Apr. 11, 2023

(54) ADJUSTABLE HEARING PROTECTION DEVICE

(71) Applicant: Arjen Teake De Jong, Barneveld (NL)

(72) Inventors: Arjen Teake De Jong, Barneveld (NL); Richard Vincent Armin De Jong, Barneveld (NL)

(73) Assignee: Arjen Teake De Jong, Barneveld (NL)

( * ) Notice: Subject to any disclaimer, the term of this patent is extended or adjusted under 35 U.S.C. 154(b) by 959 days.

(21) Appl. No.: 16/342,128

(22) PCT Filed: Oct. 16, 2017

(86) PCT No.: PCT/NL2017/050675
§ 371 (c)(1),
(2) Date: Apr. 15, 2019

(87) PCT Pub. No.: WO2018/070876
PCT Pub. Date: Apr. 19, 2018

(65) Prior Publication Data
US 2019/0254877 A1    Aug. 22, 2019

(30) Foreign Application Priority Data
Oct. 14, 2016  (NL) .................................... 2017626

(51) Int. Cl.
*A61F 11/10* (2006.01)
*G10K 11/16* (2006.01)
(Continued)

(52) U.S. Cl.
CPC .............. *A61F 11/10* (2013.01); *A61F 11/08* (2013.01); *G10K 11/16* (2013.01); *G10K 11/18* (2013.01); *A61F 11/12* (2013.01)

(58) Field of Classification Search
CPC ................ H04R 1/1083; H04R 1/2876; H04R 1/1016; H04R 1/105; H04R 1/1041; H04R 25/60;
(Continued)

(56) References Cited

U.S. PATENT DOCUMENTS 4,311,206 A * 1/1982 Johnson ................. H04R 25/48
381/328
5,332,871 A * 7/1994 Carrigan ................. A61F 11/08
181/135

(Continued)

FOREIGN PATENT DOCUMENTS

EP      0955025 A1    11/1999
FR    2997010 A1 *    4/2014     .............. A61F 11/06
(Continued)

*Primary Examiner* — Ophelia A Hawthorne
*Assistant Examiner* — Michael Milo
(74) *Attorney, Agent, or Firm* — Myers Wolin, LLC

(57) ABSTRACT

The present invention relates to an adjustable hearing protection device for arranging in and/or on the ear, the hearing protection device including: a housing with an acoustic entrance opening, an insertion part for inserting into an auditory canal of the ear extending from the housing with an acoustic exit opening oriented toward the interior of the auditory canal, and adjusting means for adjusting the hearing protection device to one of at least two acoustic adjustment positions. Each acoustic adjustment position sets one of a number of acoustic couplings between the entrance opening and the exit opening.

26 Claims, 15 Drawing Sheets

(51) Int. Cl.
    *G10K 11/18*     (2006.01)
    *A61F 11/08*     (2006.01)
    *A61F 11/12*     (2006.01)

(58) Field of Classification Search
    CPC ............... H04R 25/652; H04R 25/658; H04R 2460/11; A61F 11/08; A61F 11/10; A61F 11/12; A61F 11/006; A61F 2011/085; A61F 11/30; G10K 11/16; G10K 11/18
    USPC ......... 128/864, 865, 867; 181/135; 381/321, 381/328
    See application file for complete search history.

(56) References Cited

U.S. PATENT DOCUMENTS

| | | |
|---|---|---|
| 6,082,485 A | 7/2000 | Smith |
| 6,148,821 A | 11/2000 | Falco |
| 2003/0159878 A1* | 8/2003 | Hakansson ............ A61F 11/08 181/135 |
| 2005/0087195 A1* | 4/2005 | Huang ................... A61F 11/12 128/864 |
| 2007/0183606 A1* | 8/2007 | Doty ..................... A61F 11/12 381/72 |
| 2008/0276945 A1* | 11/2008 | Rosen ................... A61F 11/08 128/864 |
| 2011/0158421 A1* | 6/2011 | Voix ..................... A61F 11/08 381/72 |
| 2012/0318605 A1 | 12/2012 | Brown |
| 2014/0190494 A1* | 7/2014 | Ely ....................... A61F 11/12 128/868 |
| 2016/0309266 A1* | 10/2016 | Olsen ................. H04R 25/305 |
| 2017/0202710 A1* | 7/2017 | van 'T Hof ............ A61F 11/08 |

FOREIGN PATENT DOCUMENTS

| | | |
|---|---|---|
| FR | 2997010 A1 | 4/2014 |
| WO | 2009086649 A1 | 7/2009 |

\* cited by examiner

ADJUSTABLE HEARING PROTECTION DEVICE

CROSS-REFERENCE TO RELATED APPLICATIONS

This application is the United States national phase of International Application No. PCT/NL2017/050675 filed Oct. 16, 2017, and claims priority to Dutch Patent Application No. 2017626 filed Oct. 14, 2016, the disclosure of each of which is hereby incorporated by reference in its entirety.

BACKGROUND OF THE INVENTION

Field of the Invention

The present invention relates to an adjustable hearing protection device for arranging in and/or on the ear for the purpose of providing a number of distinct settings for the measure of protection of the ear.

Technical Considerations

The use of earplugs to protect hearing is known. Many types of protection by means of earplugs have been developed. Simple forms of protection provided a certain measure of damping of ambient sound by blocking the auditory canal of the ear. Such a blockage also distorts the sound, whereby the origin of the sound is less readily discernible by the user.

This is however a drawback when listening to music or voices since high quality is usually desired when listening to music or voices even when these are reproduced loudly. Earplugs have therefore been developed in which a partially continuous air channel is realized by means of filters in that the filter comprises a diaphragm with a small opening. Hereby realized on the one hand is a high degree of damping and on the other that the sound is transmitted with certain quality.

The present inventor has established that such an operating principle also has a drawback. Such an earplug is not able to modify the damping to changing conditions. When the user moves from a space with a very high sound level to a space with a very low sound level while wearing an earplug with a high damping, and thereby a greater protection, the user cannot then function properly in the space with the low sound level because the damping is too high to allow passage of the low sound level. The drawback here is that the wearer has to alternate insertion and removal of the earplug in order to adapt to the conditions.

SUMMARY OF THE INVENTION

In order to obviate such a drawback the present invention provides an adjustable hearing protection device for arranging in and/or on the ear, the hearing protection device comprising:

a housing with an acoustic entrance opening, an insertion part for inserting into an auditory canal of the ear extending from the housing with an acoustic exit opening oriented toward the interior of the auditory canal, adjusting means for adjusting the hearing protection device to one of at least two acoustic adjustment positions, wherein each acoustic adjustment position sets one of a number of acoustic couplings between the entrance opening and the exit opening.

A first important advantage of such a hearing protection device is that it is adaptable to conditions where a high damping is desired and conditions where a low damping is desired. An example hereof is a hearing protection device with four adjustment positions, a very high damping, a high measure of damping, a moderate damping and a position without damping. Using such a hearing protection device set to the high protection adjustment position a user can enter a space with a high sound intensity without damaging his/her hearing. By applying a suitable filter a high degree of sound quality can be realized here with a high measure of damping. When leaving the space and arriving in a space with a low sound level where the user has to focus on voices, he/she can easily modify the adjustment position in order to be easily able to understand the voices in a position with low damping or no damping.

In a first preferred embodiment the adjusting means in the hearing protection device comprise a revolver, which revolver can be positioned rotatably so as to correspond to each adjustment position. It hereby becomes possible in simple manner to adjust the hearing protection device by means of a rotating turning movement of the revolver. Since the hearing protection device is situated at the ear, it can easily be reached with the hand so as to easily perform the turning movement. In alternative manner the adjusting means comprise a slide, which slide can be positioned slidably so as to correspond to each adjustment position. Depending on the preference of the user, such a movement can be performed easily for the purpose of setting the adjusting means.

According to a further preferred embodiment, each acoustic coupling is provided by a predetermined combination of at least one filter and/or at least one channel configuration. Provision is for instance made that the same filter or channel part can be applied in different acoustic couplings when they are arranged in series or in parallel in each respective acoustic coupling.

At least one of the at least one filter is preferably arrangeable here in the housing. In alternative manner at least one of the at least one filter is arrangeable in the adjusting means. In an embodiment in which one or more filters are arranged in the revolver, they provide, together with filters and/or channel parts of the housing, an acoustic coupling when they are arranged coupled acoustically in an adjustment position.

In a further preferred embodiment at least one of the acoustic couplings provides a substantially unobstructed acoustic passage for sound. A variant with a position with substantially normal hearing function is possible by applying such a preferred embodiment.

In alternative manner the hearing protection device more preferably provides in at least one of the acoustic couplings an acoustic coupling configured to simulate or substantially simulate an acoustic coupling such as is provided by an empty auditory canal. The human auditory canal provides a determined acoustic coupling between the eardrum and the surrounding area. This acoustic coupling serves to provide a resonance for the purpose of providing an amplification of determined frequencies, particularly in the range between 2000 and 4000 Hz.

A hearing protection device according to the present invention disrupts this natural resonance in the auditory canal just as any blockage or partial blockage of the auditory canal would do. The present preferred embodiment obviates such a drawback by simulating this natural resonance in the hearing protection device by providing one or more resonance spaces therein. Within the context of the present description these resonance spaces can be modified experimentally to the ear, and more preferably take into account the remaining part of the auditory canal for the purpose of providing the most natural possible reproduction to the eardrum. At least one of the acoustic couplings more preferably comprises a Helmholtz resonator. A Helmholtz generator is a space for resonance with a certain volume with two openings arranged substantially opposite each other, an entrance opening and an exit opening of the chamber.

According to a further preferred embodiment, the device comprises acoustic channel parts and/or filters arranged serially and/or parallel relative to each other. Predetermined combinations of acoustic couplings are hereby arrangeable in the housing and/or adjusting means.

For the purpose of providing a desired damping effect the at least one filter provides a damping effect on the acoustic coupling by means of a narrowest part of a channel passage with a length greater than the diameter, preferably greater than twice the diameter, more preferably greater than four times the diameter, more preferably greater than five times the diameter, more preferably greater than ten times the diameter. By means of this measure the present inventor identifies in experimental manner a relation between the length of the channel and the damping effect, whereby the inventor disassociates himself from a damping effect by means of a substantially pointed narrowing of the passage. The present inventor provides a relatively long channel with a relatively large cross-section for the purpose of providing a similar damping with a very short cut-off point with a very small diameter.

The entrance opening more preferably comprises a substantially cone-shaped or horn-shaped member for receiving a sufficient amount of sound to provide sufficient quality following damping thereof.

According to a further preferred embodiment, the adjusting means, preferably the substantially cone-shaped or horn-shaped member, in the hearing protection device comprise biasing means, such as a deformable wall part, for imparting a bias to a wall part comprising a passage opening for sound for the purpose of moving this passage opening to the position of an acoustic coupling to be selected. Because the wall part comprising a passage opening is brought under bias by biasing means, leakage of sound other than via the selected acoustic coupling can be impeded or prevented. The quality of the selected acoustic coupling is hereby enhanced.

According to a further preferred embodiment, a wall part of the adjusting means, such as comprising the passage opening, is congruent with a wall part of the housing whereby this wall part of the adjusting means provides an acoustic seal for at least one acoustic coupling other than the adjusted acoustic coupling. Leakage of sound other than via the selected acoustic coupling is hereby also impeded or prevented.

It is particularly advantageous to apply the bias in combination with the congruity of said wall parts. The congruent wall of the adjusting means is pressed here under bias against the congruent wall of the housing, thereby preventing in optimal manner the separation of the acoustic couplings and other leakages of sound.

In a further preferred embodiment at least one acoustic coupling more preferably comprises an elongate channel which is preferably formed as a channel through a solid body, more preferably by means of a hose through a hollow space. Such an elongate channel provides the advantage that a reliable and considerable acoustic damping is provided with good results. This is possible because sufficient space is available herefor in the housing of the hearing protection device according to the present invention and/or preferred embodiment, this in contrast to a hearing protection device with a substantially short straight channel placed axially in the auditory canal. The filters required for such protection having a short channel suitable therefor with a cross-section of substantially a tenth of a millimetre or less for a sufficient damping are therefore replaceable by the elongate channels as described in this document.

More preferably provided is a preferred embodiment with two acoustic adjustment positions and two acoustic couplings. These are preferably disposed in a sliding arrangement.

According to a further preferred embodiment, the hearing protection device comprises indicator means discernible by touch for discerning at least one adjustment position by feel. The acoustic coupling is hereby always provided in reliable manner by correctly reaching the associated adjustment position. This takes place in a manner which is easy for the user to discern outside the field of vision of the user.

The device more preferably comprises at least one intermediate stop position for the purpose of providing positioning of the adjusting means relative to an acoustic adjustment position. The adjusting means are hereby held in an adjustment position in advantageous manner.

According to a further preferred embodiment, a support member is oriented substantially upward for the purpose of engaging an edge of the external ear when the hearing protection device is arranged in the ear. This engagement on an edge of the external ear contributes toward a stable 'seating' of the device in the ear.

The hearing protection device more preferably comprises individually, or in combination with the support member, an ear contact surface on the underside for supporting thereof by parts of the ear on the underside of the hearing protection device when it is arranged in the ear. Preferably in combination the support member and the ear contact surface on the underside provide, preferably in further combination with the insertion part, the said stable 'seating' in an ear as a whole. Through the distribution of contact this placing in the ear also provides a high degree of comfort when the hearing protection device is arranged in the ear.

Tactile indication and/or the intermediate stop position is for this purpose provided in advantageous manner by magnetic action.

The housing more preferably comprises a receiving chamber for receiving an adjustable element of the adjusting means, and wherein the adjusting means comprise the adjustable element for arrangement thereof at the receiving chamber of the housing, wherein the adjustable element comprises the entrance opening and a passage opening for coupling thereof for the purpose of forming, in co-action with the housing, an acoustic coupling associated with an acoustic adjustment position. A device is hereby provided which can be manufactured advantageously, wherein the housing and the adjustable element can be manufactured in advantageous manner by means of for instance a forming process such as injection moulding.

The device more preferably comprises a support member or positioning member for providing a supporting or positioning effect relative to the ear. The device can hereby be positioned firmly in trustworthy manner, and the user can for instance easily set the adjusting means to another setting. The adjusting means preferably comprise a control edge for operation thereof, wherein the control edge is preferably substantially annular and protrudes from the ear during use in a manner such as to be substantially engageable by two fingers.

According to a further preferred embodiment, the entrance opening is arranged in a side of the adjusting means, or control edge, remote from the head.

BRIEF DESCRIPTION OF THE DRAWINGS

Further advantages, features and details of the present invention will be described in greater detail hereinbelow on the basis of one or more preferred embodiments with reference to the accompanying figures. Similar, though not necessarily identical components of different preferred embodiments are designated with the same reference numerals.

FIGS. 1-6B show a number of views of a first preferred embodiment according to the present invention.

DESCRIPTION OF THE INVENTION

Figure 1:
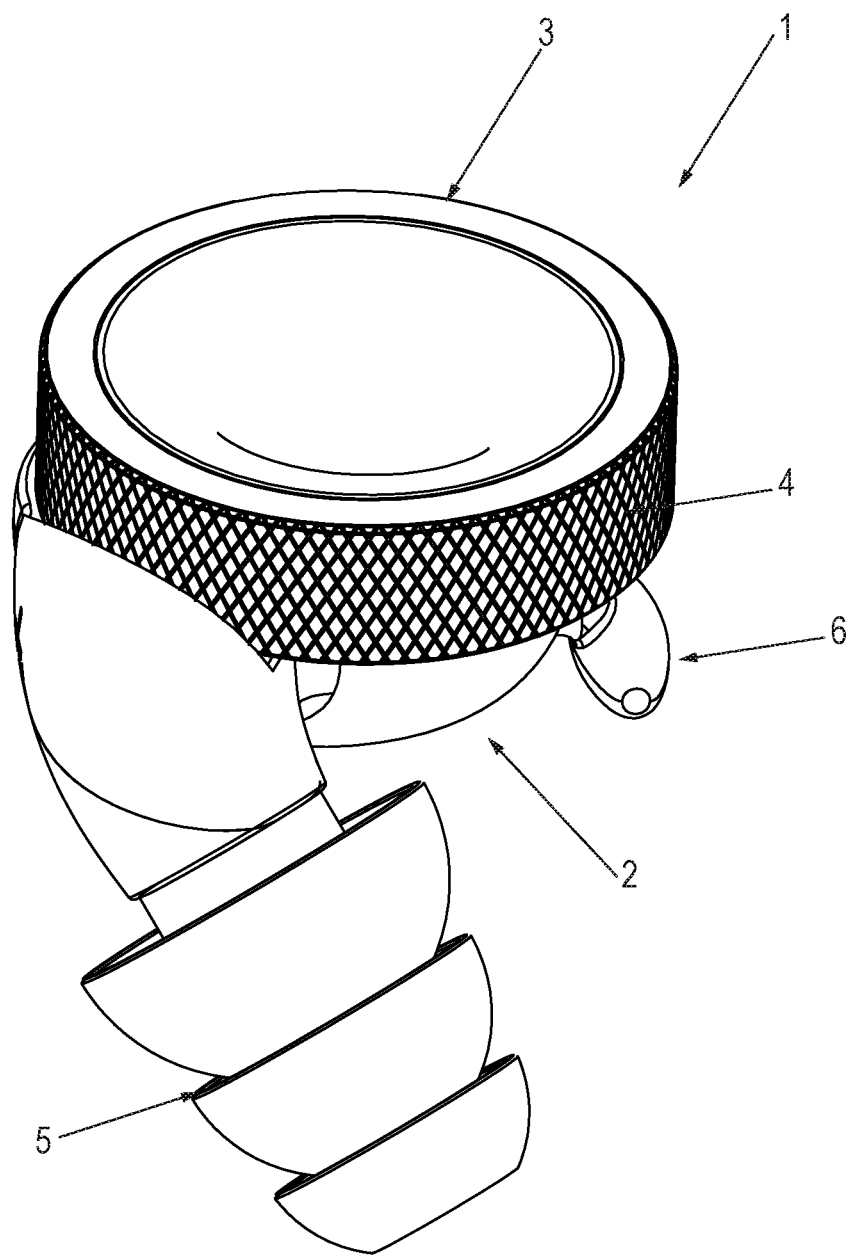
Figure 2:
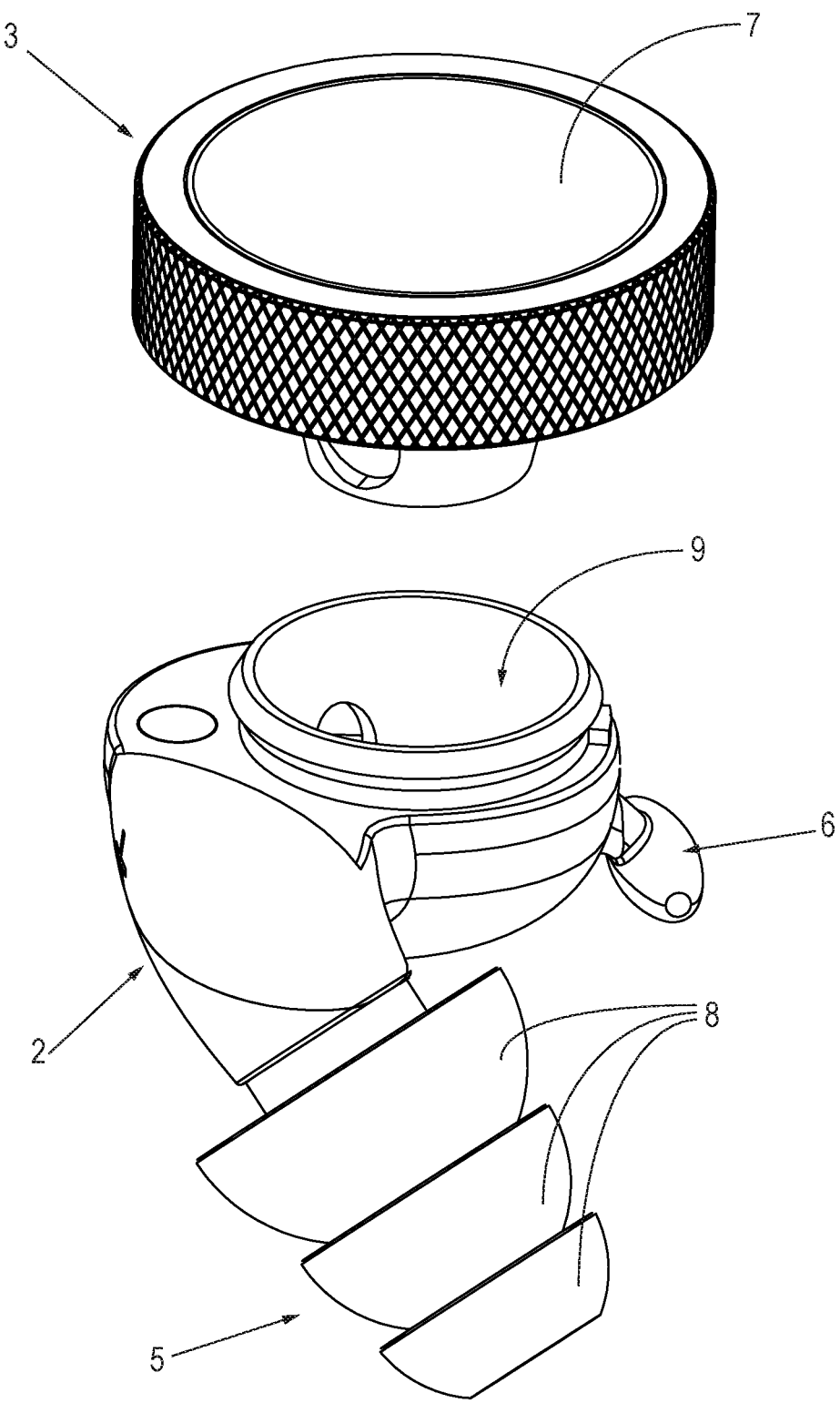
Figure 3:
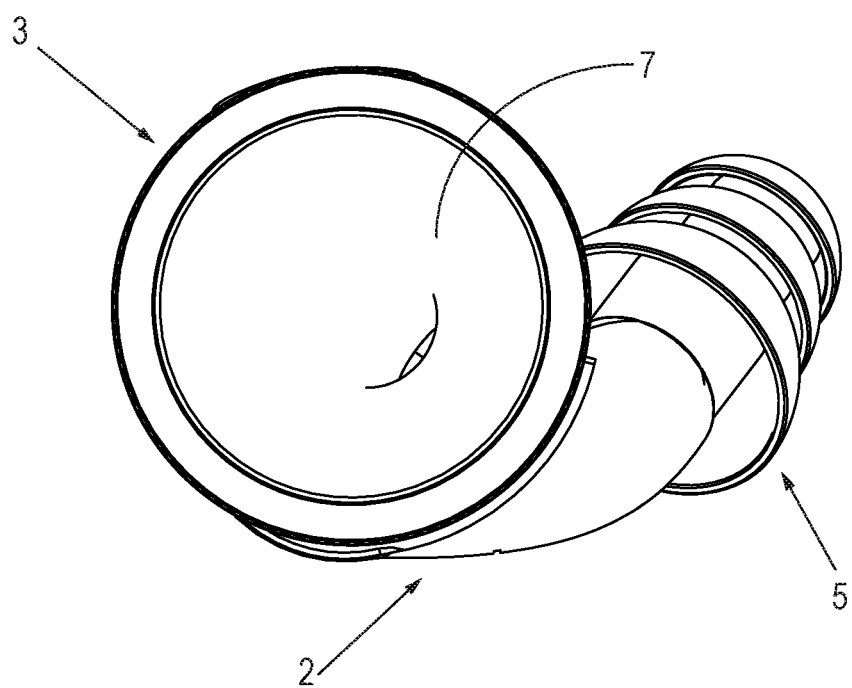
Figure 4:
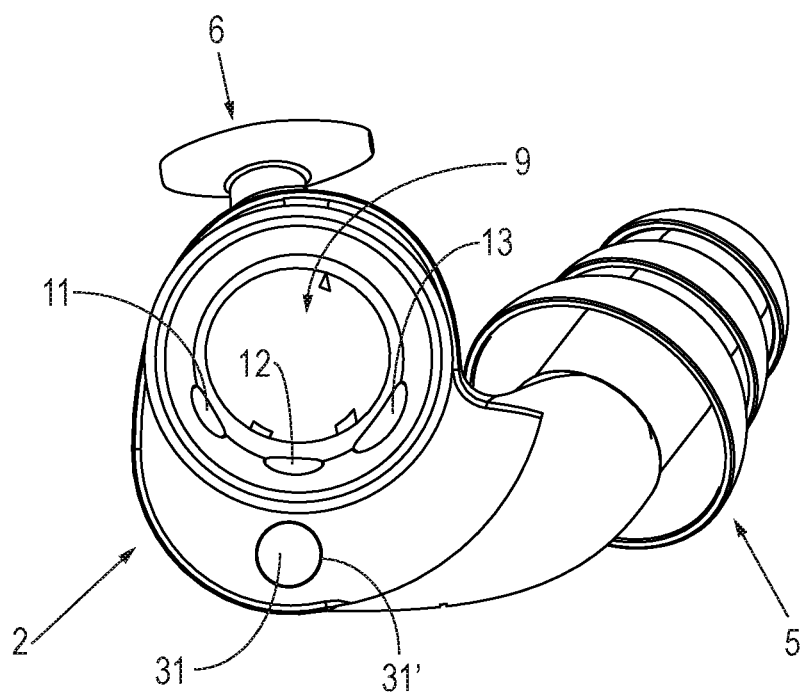
Figure 5:
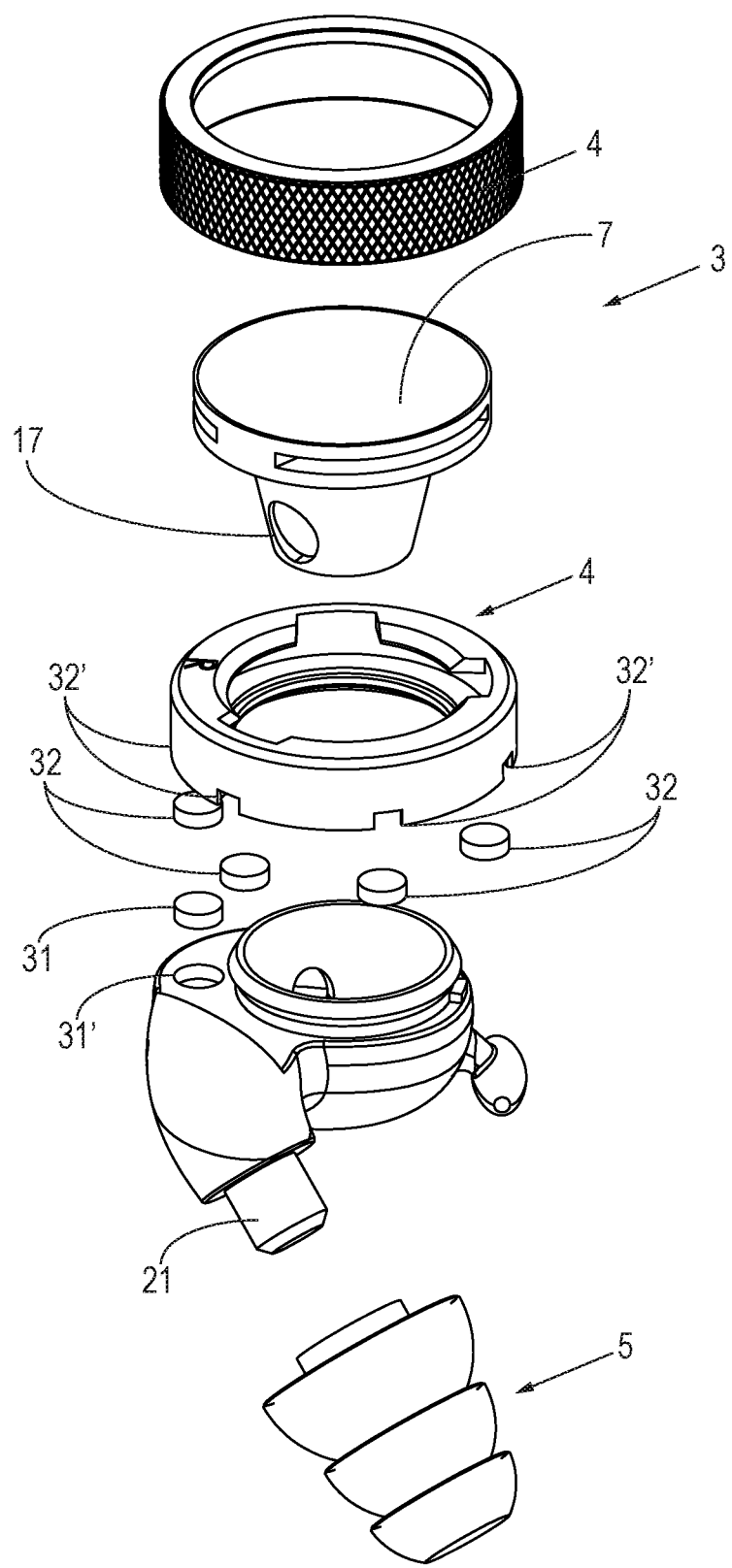
Figure 6:
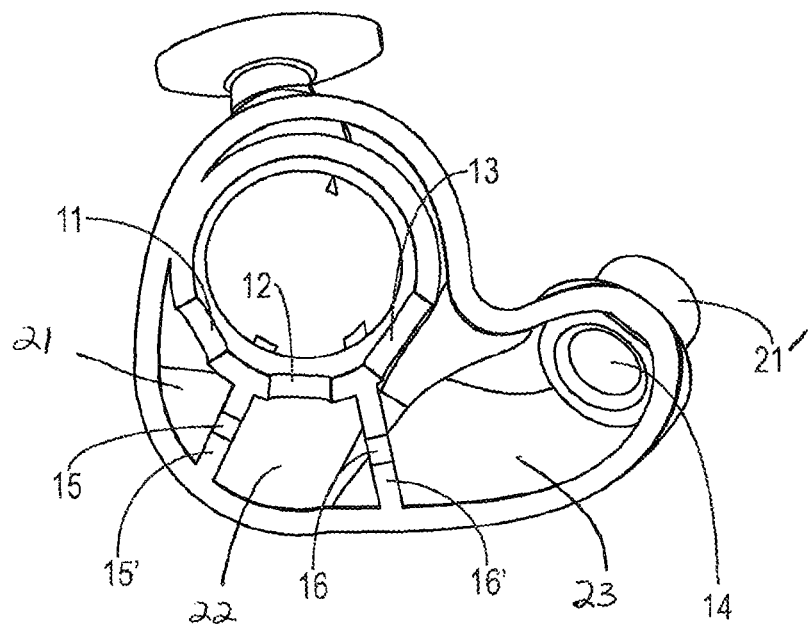
Figure 6:
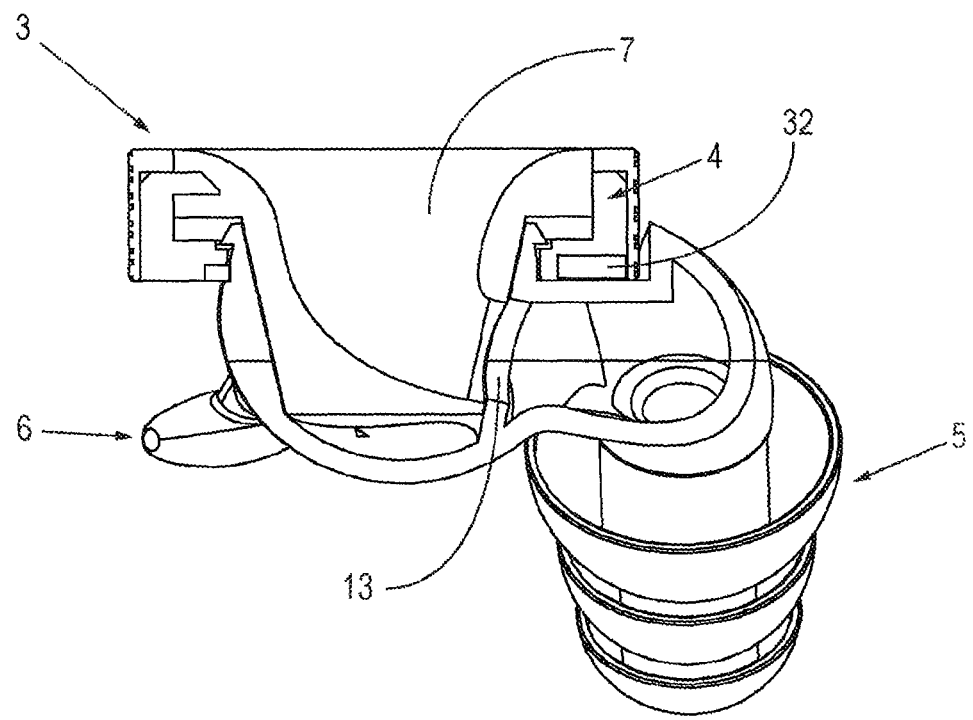

A first preferred embodiment (FIG. 1) according to the present invention relates to an adjustable hearing protection device 1. This comprises a housing 2 with an auditory canal element 5 arranged thereon for arrangement thereof in an auditory canal during wearing of hearing protection device 1. A substantially zeppelin-shaped support element 6 is also arranged on the ear side of the housing.

The housing comprises a receiving space 9 for receiving adjusting means 3 therein. Adjusting means 3 are embodied as a rotatable cone 7 with an operating ring 4 arranged thereon. The rotatable cone 7 forms the entrance opening of the hearing protection device and comprises a passage opening 17 for passage of sound in the direction of inlet openings 11, 12, 13 of the housing.

The shortest path for the sound through the housing runs through opening 13 via space 23 to opening 14 in the direction of the auditory canal. A slightly longer path for the sound through the housing runs through opening 12 via space 22 and subsequently via space 23 through opening 16 through wall 16' to space 23 and further. The longest path in this preferred embodiment runs through opening 11 via space 21 through opening 15 through wall 15' in the direction of space 22 and further.

Provided in openings 15, 16 are filters (not shown) for imparting additional damping. Provision is also made that placing of filters is possible in openings 11, 12, 13 and 14. The skilled person will configure the placing of these filters and the damping effect thereof within the context of the present invention and the desired acoustic couplings. Each of these filters is therefore optional within the context of the present invention.

In the housing a magnet 31 is also arranged in opening 31' for co-action with respective magnets 32 arrangeable in openings 32' of the adjusting means. A positioning of the cone with the opening 17 relative to respective openings 11, 12, 13 is hereby realizable in tactile manner. Through the action of the magnets relative to each other the adjusting means remain positioned at the adjustment position. Provision is alternatively made that the positioning is realized by means of notches and balls placed under bias.

The cone is preferably manufactured in a manner such that the connection to the housing is sound-proof.

Figure 7:
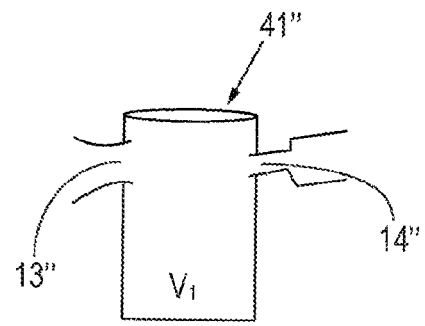
FIG. 7 shows a schematic representation of a Helmholtz generator.
Figure 8:
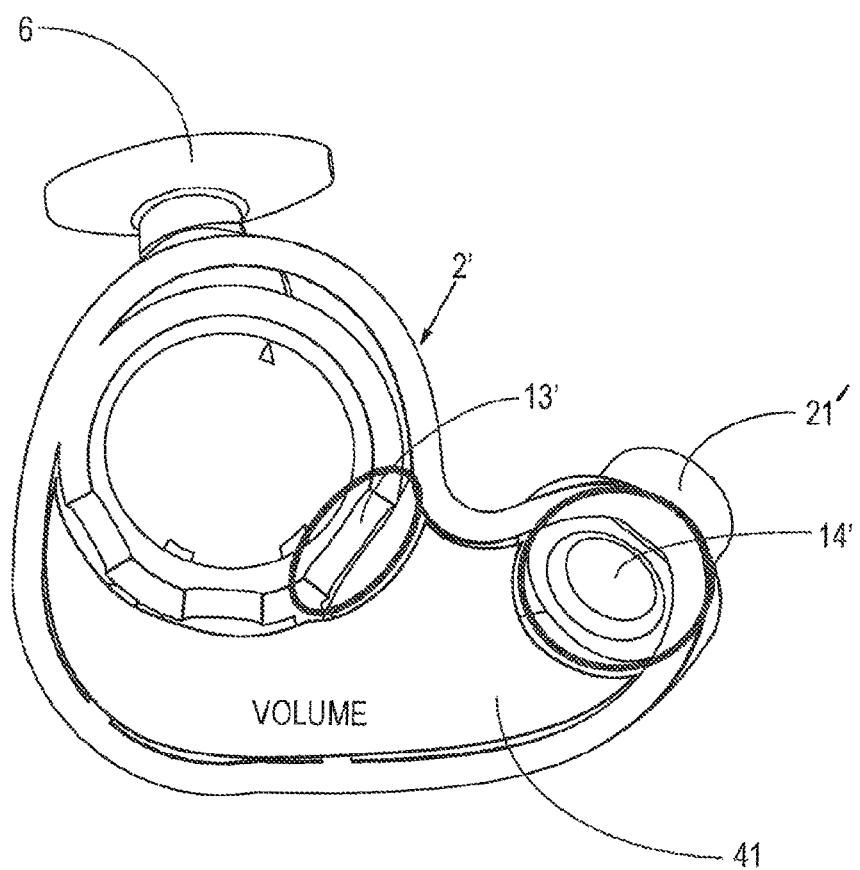
FIG. 8 shows a schematic view of a further preferred embodiment comprising a Helmholtz generator.

FIG. 7 shows the operation of a Helmholtz resonator, wherein a space 41" is provided with an inlet opening 13" and an outlet opening 14". Provided in similar manner in the preferred embodiment according to FIG. 8 is a Helmholtz generator space 41 with two respective openings 13', 14' arranged opposite each other analogously with the openings of an above preferred embodiment. A Helmholtz resonator can be arranged in the device in this way.

Figure 9:
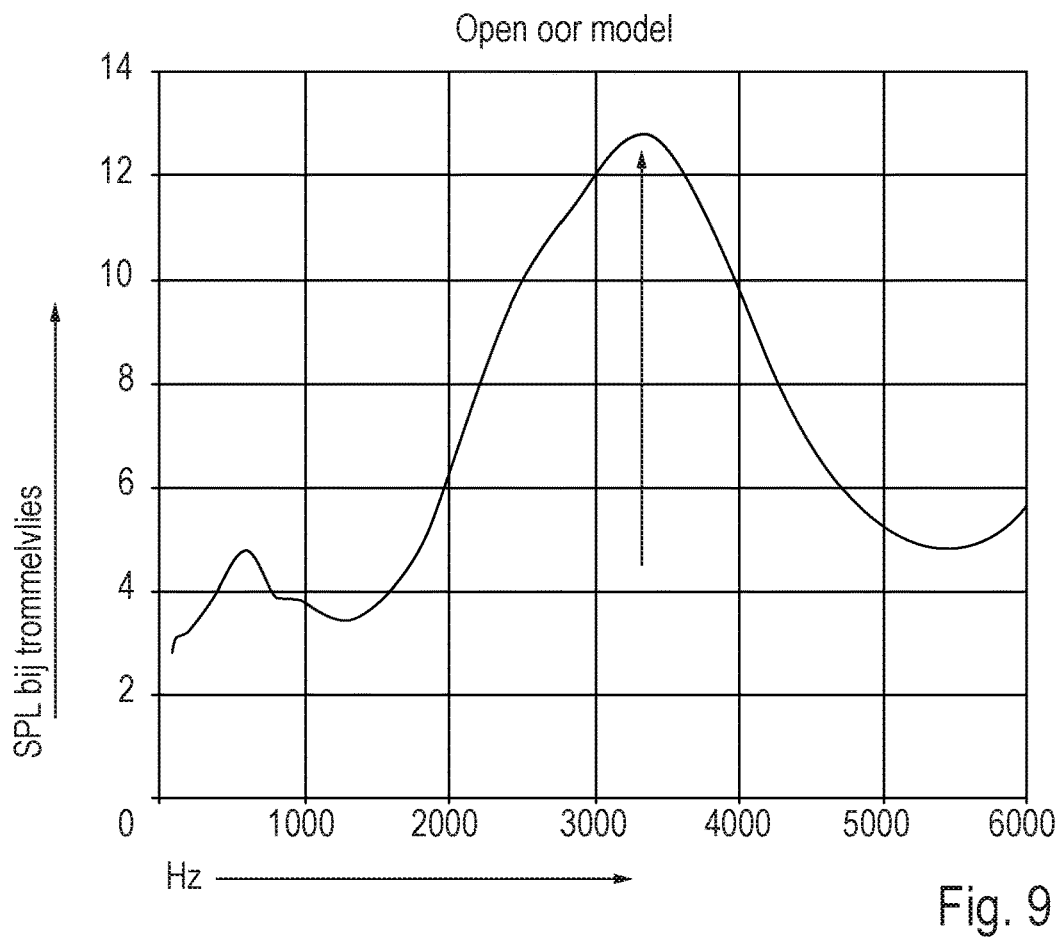
FIG. 9 shows a graphic representation of resonance in a natural auditory canal for simulation thereof by means of a device according to the present invention.

Shown graphically in FIG. 9 is how a natural auditory canal provides frequencies to the eardrum within the range of 2000-4000 Hz with a considerably higher sound volume than lower and higher frequencies. Provision is made that such a resonance is simulated by preferred embodiments according to the present invention.

Figure 10:
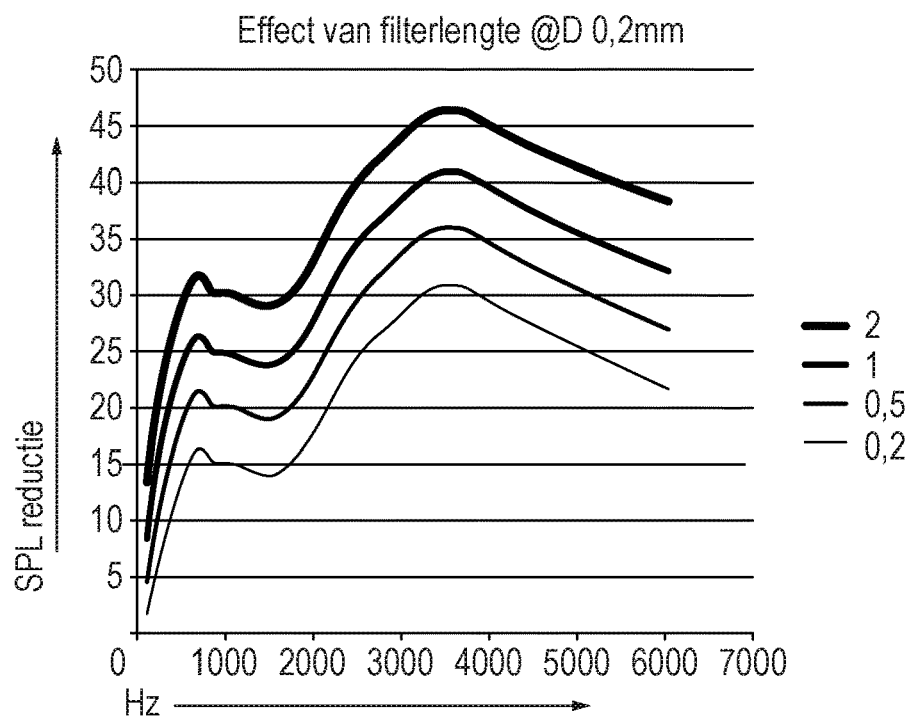
FIG. 10 shows a graphic representation of damping effects related to a diameter and a length of a filter channel.

Shown in FIG. 10 is how the sound damping is realized by applying a filter with a diameter of 0.2 mm with a respective length of 0.2 mm, 0.5 mm, 1 mm, 2 mm.

The auditory canal element 5 is arrangeable on a flange 21' and can be fitted in interchangeable manner to the ear of the user.

Figure 11:
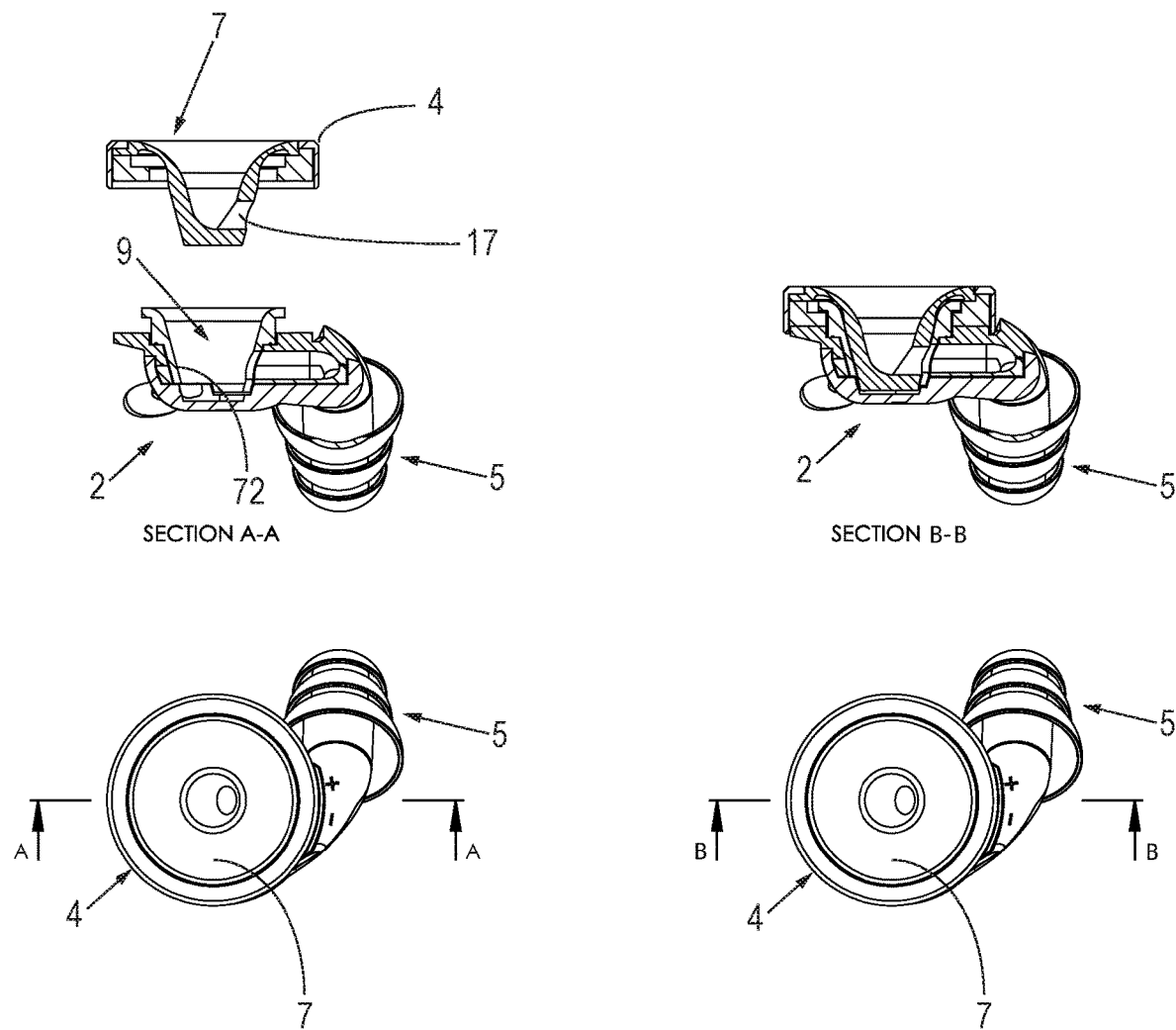
FIG. 11-17 show a number of views of a further preferred embodiment according to the present invention.
Figure 12:
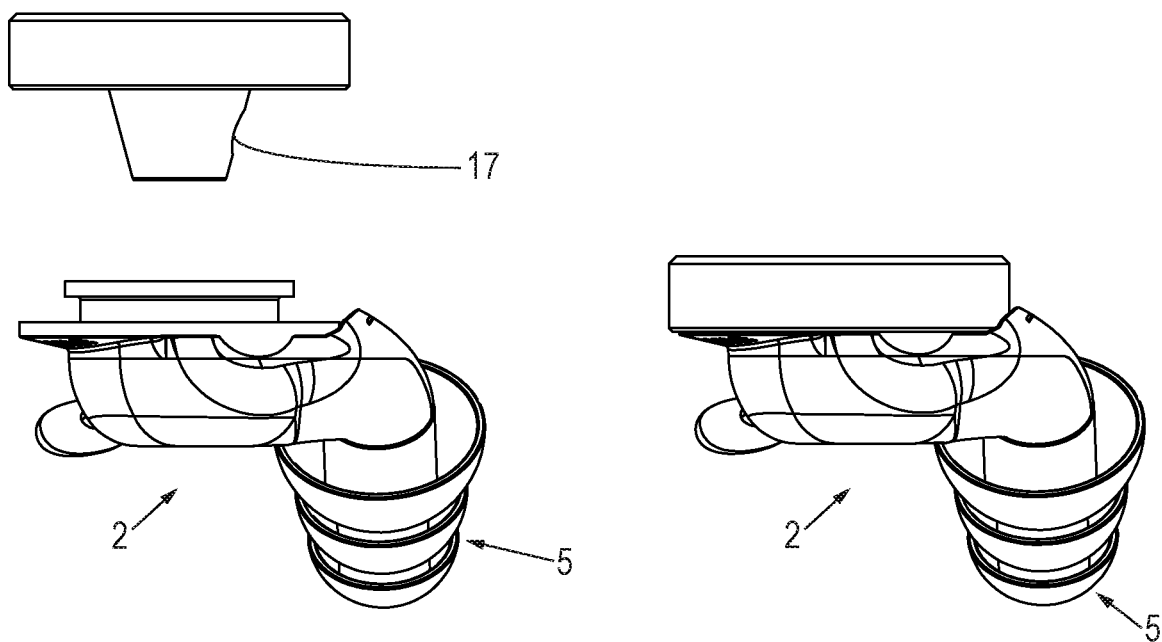
Figure 13:
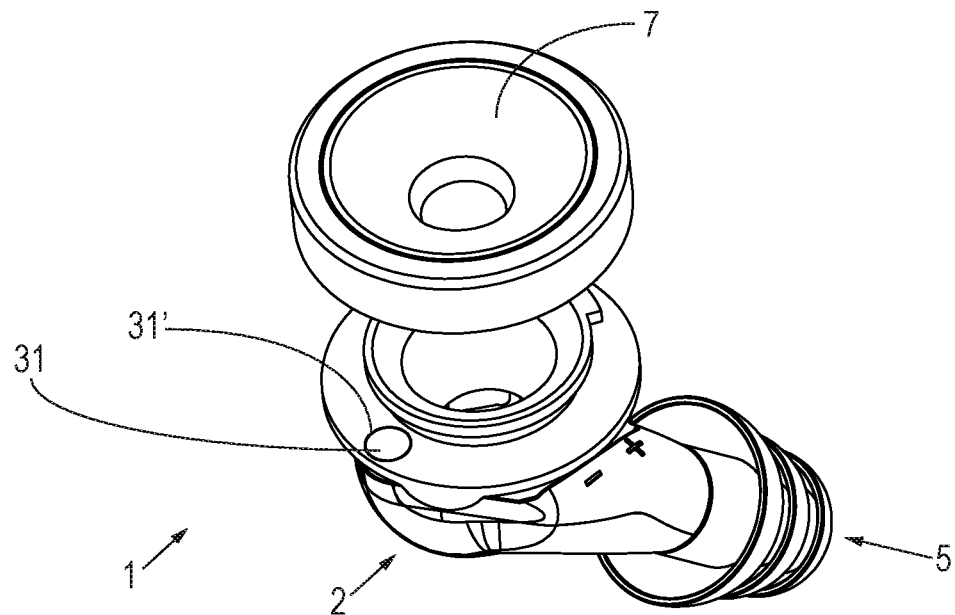
Figure 13:
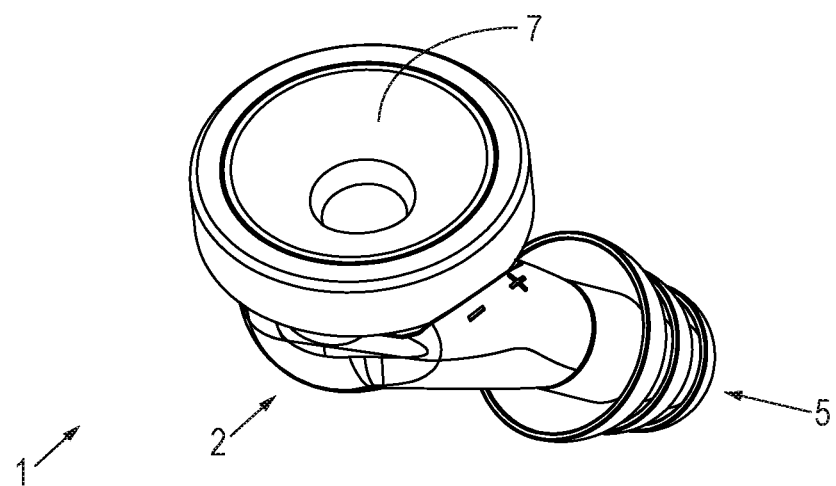
Figure 14:
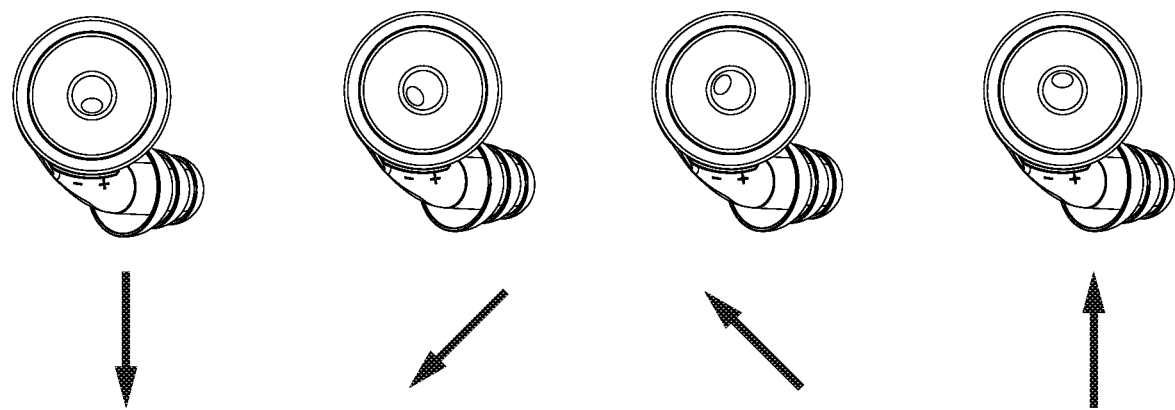
Figure 15:
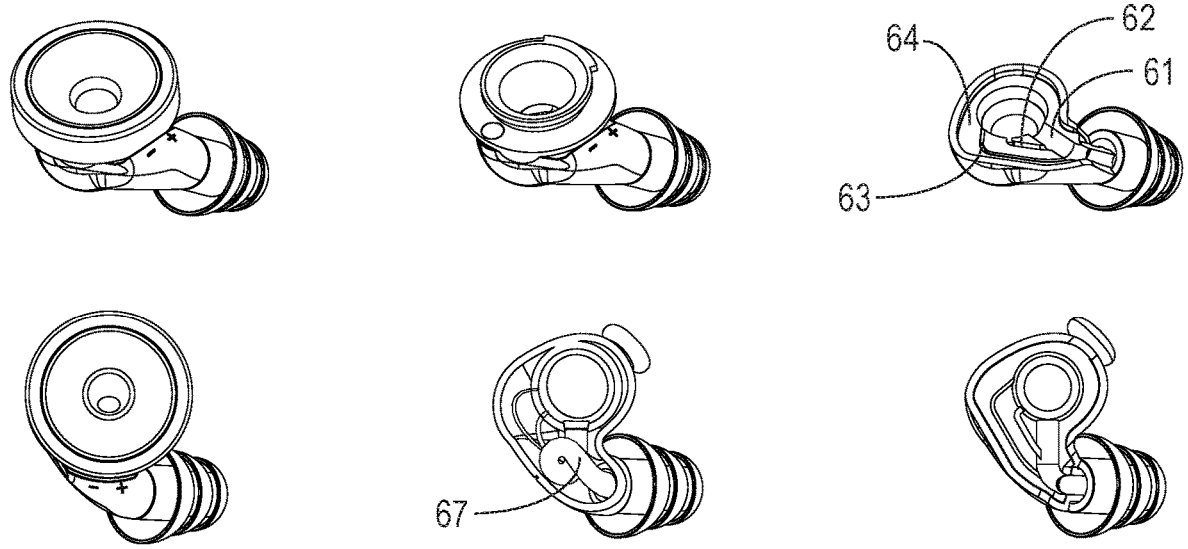
Figure 16:
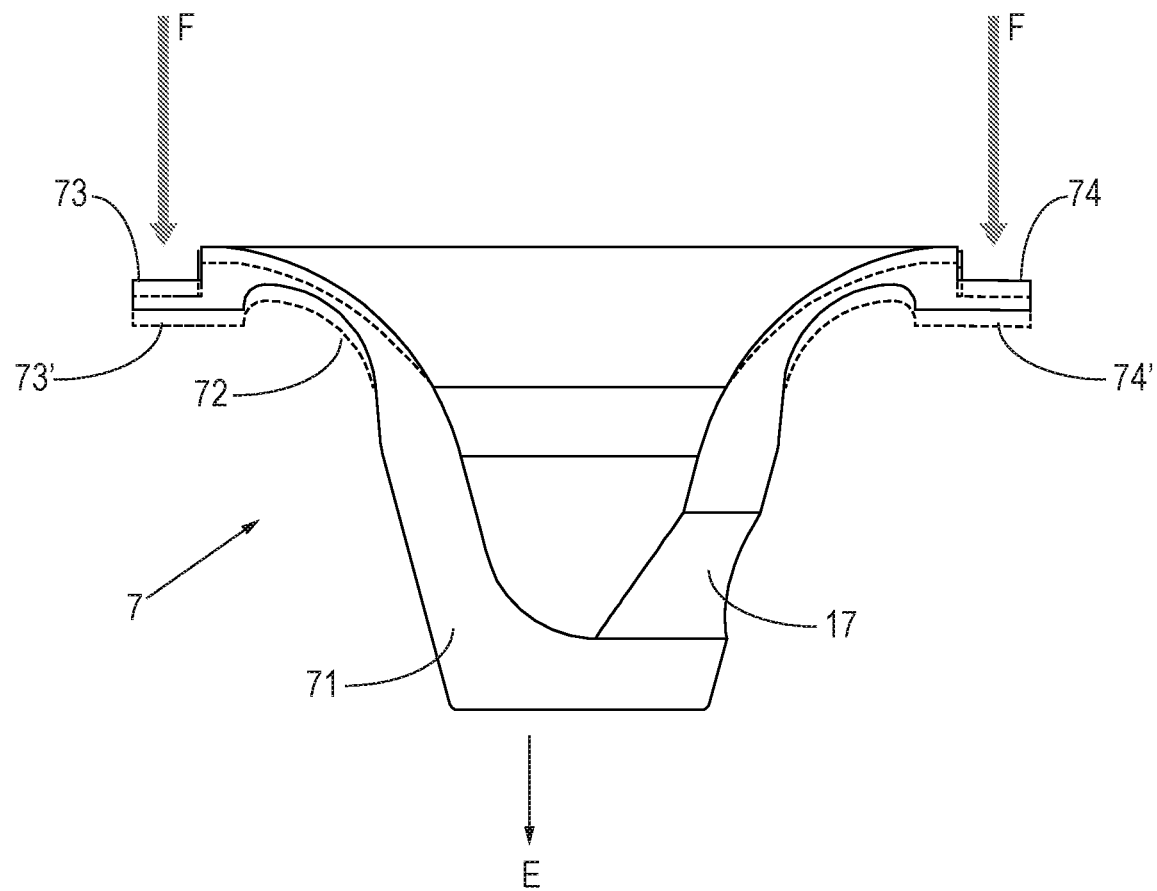

FIGS. 11 and 12 show a number of views of a further preferred embodiment according to the present invention. Also shown here is housing 2 with auditory canal element 5 for arrangement thereof in the auditory canal during wearing of hearing protection device 1.

Cone 7 is arrangeable in receiving space 9 of the housing in rotatable manner for reaching, through opening 17 of the cone, the different channels 61, 62, 63 arranged in a solid element 64 of the housing. Three acoustic couplings are defined by means of these channels 61, 62, 63. A fourth acoustic coupling provides a maximum damping and in this case does not comprise a channel.

It is important that cone 7 is formed with a lower, thicker wall part 71 with channel 17 therein, which wall part 71 is substantially rigid for connection to a wall part with the openings for the channels of the housing. A deformable wall part 72 imparts a bias in the direction of the arrow E when the wall part is pressed downward relative to wall part 71 in the direction of arrows F. Pressing elements in the natural position 73, 74 of the material are pressed downward when the cone is arranged in the housing with adjusting ring 4 arranged thereon. Pressing elements 73, 74 are hereby brought into the positions 73', 74' relative to wall part 71. The resulting biasing force provides a sustained close connection of wall part 71 to a corresponding wall part 77 of the housing.

A suitable choice of material for the cone, such as a rubber-like material such as TPE, ensures in combination with the bias that the cone is both sealing and readily rotatable. An easy rotatability is advantageous in the device when it is arranged in the ear for the purpose of user convenience and comfort, in addition to the proper separation of the acoustic couplings and preventing leakage of sound via the acoustic couplings.

The acoustic coupling which makes use of channel 61 provides the freest passage of sound and is preferably such that voice sound is reproduced as neutrally as possible. It is hereby possible to temporarily speak to people in the vicinity by selecting this acoustic coupling.

A channel 67 is suitable to serve as a Helmholtz generator for a relative amplification of sounds in the range of 2 kHz to 6 kHz, such as the speech range of frequencies.

Figure 17:
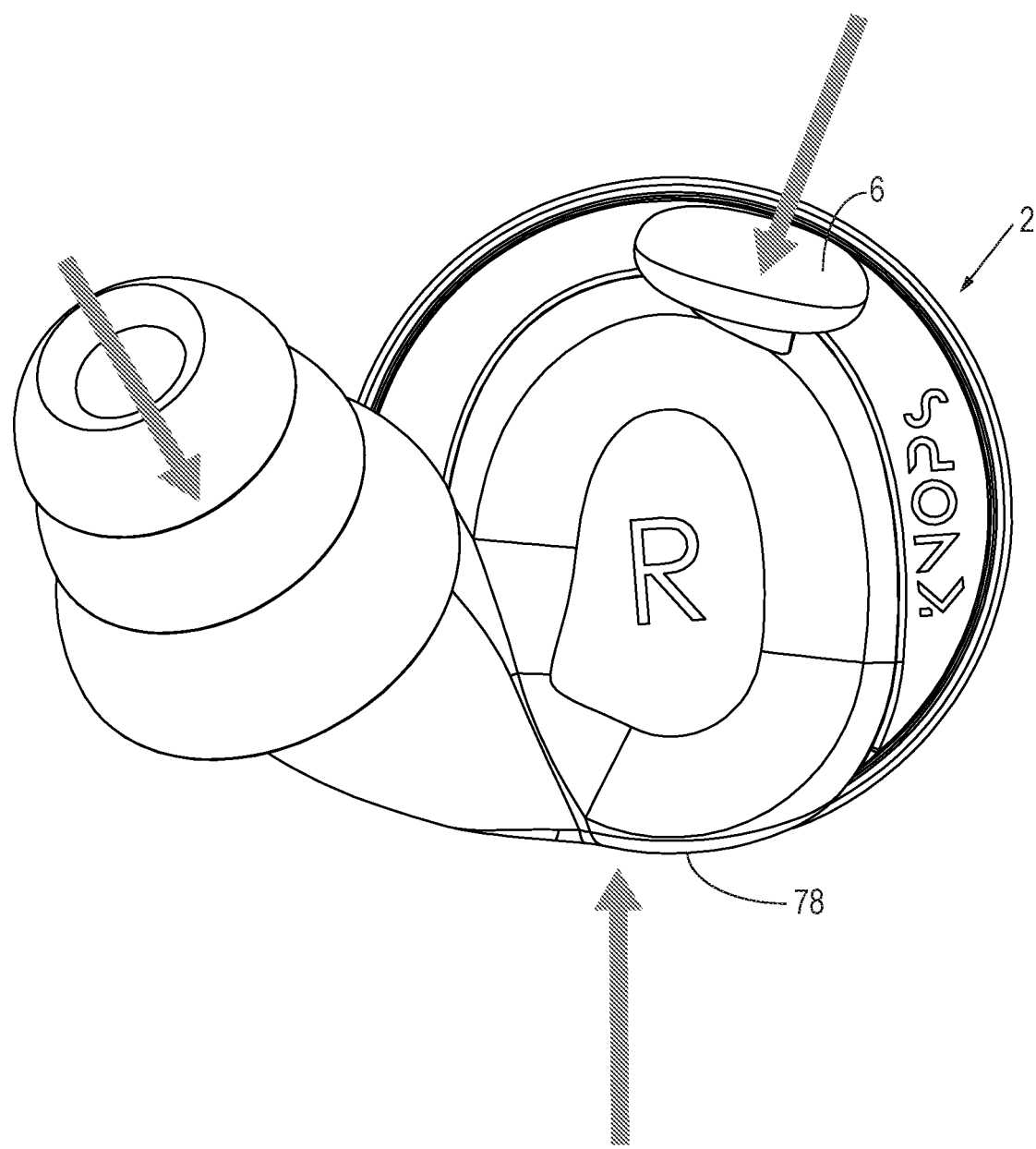
Figure 18:
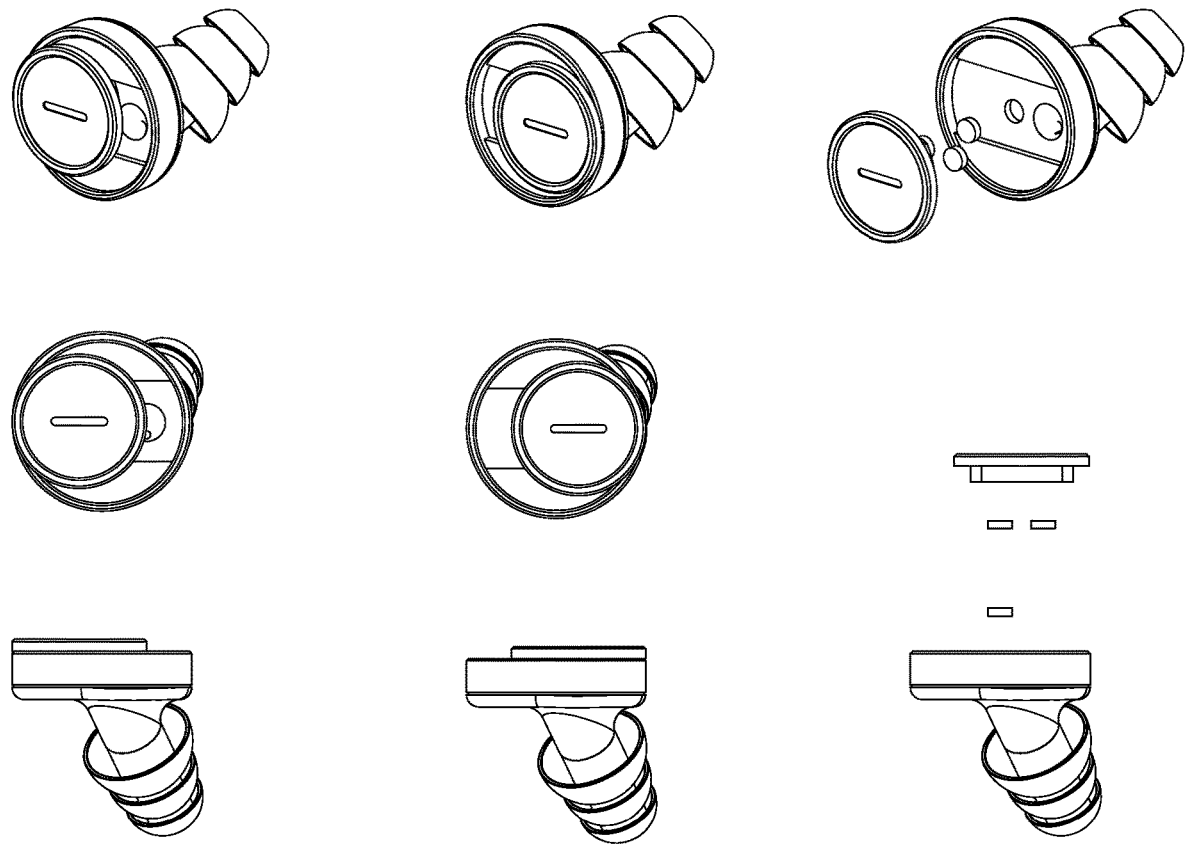
FIG. 18 shows a number of views of a further preferred embodiment according to the present invention.

FIG. 17 shows the contact points with the ear, such as support element 6, insertion member 5 and a contact surface 78 for contact with the interior of the ear, substantially opposite support element 6. Placing of any element in the ear is hereby possible in advantageous manner. In addition to a hearing protection device, an ear part with a sound provision is likewise provided here.

The present invention has been described in the foregoing on the basis of several preferred embodiments. Different aspects of different embodiments are deemed described in combination with each other, wherein all combinations which can be deemed by a skilled person in the field as falling within the scope of the invention on the basis of reading of this document are included. These preferred embodiments are not limitative for the scope of protection of this document. The rights sought are defined in the appended claims.

The invention claimed is:

1. An adjustable hearing protection device for arranging in and/or on an ear, the hearing protection device comprising:
   a housing with an acoustic entrance opening,
   an insertion part for inserting into an auditory canal of the ear extending from the housing with an acoustic exit opening oriented toward an interior of the auditory canal, and
   an adjuster configured to adjust the hearing protection device to one of at least two acoustic adjustment positions, wherein:
   each acoustic adjustment position sets one of a number of acoustic couplings between the acoustic entrance opening and the acoustic exit opening;
   a first acoustic adjustment position connects a first acoustic coupling directly between the acoustic entrance opening and the acoustic exit opening without an intervening acoustic channel coupling between the acoustic entrance opening and the acoustic exit opening, and
   a second acoustic adjustment position connects a second acoustic coupling between the acoustic entrance opening and the acoustic exit opening via an entire space of the first acoustic coupling.

2. The hearing protection device as claimed in claim 1, wherein each acoustic coupling is provided by a predetermined combination of at least one filter and/or at least one channel configuration.

3. The hearing protection device as claimed in claim 2, wherein at least one of the at least one filter is arrangeable in the housing.

4. The hearing protection device as claimed in claim 2, wherein the at least one filter is arrangeable in the adjuster.

5. The hearing protection device as claimed in claim 2, wherein the at least one filter provides a damping effect on the acoustic coupling by a narrowest part of a channel passage having a length greater than a diameter.

6. The hearing protection device as claimed in claim 1, comprising a support member or positioning member for providing a supporting or positioning effect relative to the ear.

7. The hearing protection device as claimed in claim 6, wherein the support member is oriented upward for the purpose of engaging an edge of the external ear when the hearing protection device is arranged in the ear.

8. The hearing protection device as claimed in claim 6, comprising an ear contact surface on an underside for supporting thereof by parts of the ear on the underside of the hearing protection device when it is arranged in the ear.

9. The hearing protection device as claimed in claim 1, comprising at least one intermediate stop position for the purpose of providing positioning of the adjuster relative to one of the at least two acoustic adjustment positions.

10. The hearing protection device as claimed in claim 9, wherein tactile indication and/or the intermediate stop position is provided by magnetic action.

11. The hearing protection device as claimed in claim 1, wherein the adjuster comprises a revolver, said revolver is positioned rotatably so as to correspond to each adjustment position.

12. The hearing protection device as claimed in claim 1, wherein the adjuster comprises a slide, said slide is positioned slidably so as to correspond to each adjustment position.

13. The hearing protection device as claimed in claim 1, wherein at least one of the acoustic couplings provides an unobstructed acoustic passage for sound.

14. The hearing protection device as claimed in claim 1, wherein at least one of the acoustic couplings provides an acoustic coupling configured to simulate an acoustic coupling that is provided by an empty auditory canal.

15. The hearing protection device as claimed in claim 1, wherein at least one of the acoustic couplings comprises a Helmholtz resonator.

16. The hearing protection device as claimed in claim 1, comprising acoustic channel parts and/or filters arranged serially relative to each other.

17. The hearing protection device as claimed in claim 1, comprising acoustic channel parts and/or filters arranged parallel relative to each other.

18. The hearing protection device as claimed in claim 1, wherein the acoustic entrance opening comprises a cone-shaped member.

19. The hearing protection device as claimed in claim 1, wherein the adjuster comprises a bias configured to impart a bias to a wall part comprising a passage opening for sound for the purpose of moving the passage opening to the position of one of the number of acoustic couplings.

20. The hearing protection device as claimed in claim 1, wherein a wall part of the adjuster is congruent with a wall part of the housing whereby the wall part of the adjuster provides an acoustic seal for at least one acoustic coupling other than the adjusted acoustic coupling.

21. The hearing protection device as claimed in claim 1, wherein at least one acoustic coupling comprises an elongate channel which is formed as a channel through a solid body.

22. The hearing protection device as claimed in claim 1, comprising two acoustic adjustment positions and two acoustic couplings.

23. The hearing protection device as claimed in claim 1, comprising an indicator discernible by touch for discerning at least one adjustment position by feel.

24. The hearing protection device as claimed in claim 1, wherein the housing comprises a receiving chamber for receiving an adjustable element of the adjuster, and wherein the adjuster comprises the adjustable element for arrangement thereof at the receiving chamber of the housing, wherein the adjustable element comprises the acoustic entrance opening and a passage opening for coupling thereof for the purpose of forming, in co-action with the housing, an acoustic coupling associated with an acoustic adjustment position.

25. The hearing protection device as claimed in claim 1, wherein the adjuster comprises a control edge for operation thereof, wherein the control edge is annular and is arranged outside the ear during use in a manner such as to be substantially engageable by two fingers.

26. The hearing protection device as claimed in claim 1, wherein the acoustic entrance opening is arranged in a side of the adjuster, or a control edge, remote from a head.

* * * * *